United States Patent [19]

Anderson

[11] Patent Number: 4,736,746
[45] Date of Patent: Apr. 12, 1988

[54] METHOD OF FASTENING TISSUES

[75] Inventor: Gary Anderson, Dorchester, Mass.

[73] Assignee: Dennison Manufacturing Company, Framingham, Mass.

[21] Appl. No.: 931,311

[22] Filed: Nov. 17, 1986

Related U.S. Application Data

[62] Division of Ser. No. 722,083, Apr. 11, 1985.

[51] Int. Cl.[4] ........................ A61B 17/04; B31B 1/00
[52] U.S. Cl. .................................. 128/334 R; 227/19; 411/460
[58] Field of Search ........................ 128/334 R, 334 C; 411/460; 227/19

[56] References Cited

U.S. PATENT DOCUMENTS

| 3,875,648 | 4/1975 | Bone | 227/19 |
| 4,513,746 | 4/1985 | Aranyi et al. | 128/334 C |
| 4,627,437 | 12/1986 | Bedi et al. | 128/334 C |

FOREIGN PATENT DOCUMENTS

| 129442 | 12/1984 | European Pat. Off. | 128/334 C |
| 284898 | 3/1928 | United Kingdom | 411/460 |

*Primary Examiner*—Richard C. Pinkham
*Assistant Examiner*—Gary Jackson
*Attorney, Agent, or Firm*—George E. Kersey

[57] ABSTRACT

A method of fastening biological tissues using a fastener having two opposing heads joined by a connector. The fastener is installed by driving the heads through needles having a slotted bore. The needles are pierced through the tissues and rods are then used to drive the heads through the needle bores. The needles are removed and the heads then move against the tissue surface. The connector draws the heads inward against the tissue. The heads are provided with recesses to securely receive the rods.

12 Claims, 6 Drawing Sheets

     
FIG. 4
FIG. 5
FIG. 6
FIG. 7
FIG. 8
FIG. 9
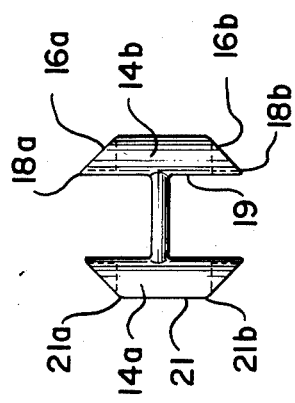
FIG. 2
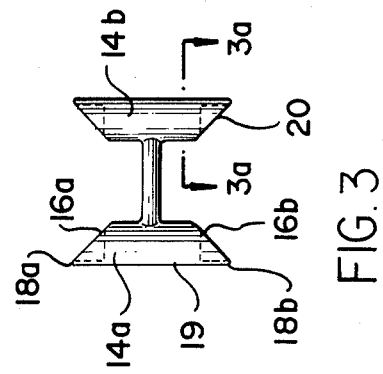
FIG. 3

METHOD OF FASTENING TISSUES

This is a division of Ser. No. 722,083, filed Apr. 11, 1985.

BACKGROUND OF THE INVENTION

This invention relates to fastening, and more particularly to methods and apparatus for the fastening of biological tissues.

A method of joining biological tissue is shown in U.S. Pat. No. 3,086,208. A U-shaped clip having barbs is applied to folded tissue layers, as for the closing of incisions. A feature of the installed clip is that it juts out from the joined area. This can be disadvantageous for fastening internal tissues because the clip could extend into interstitial areas between the fastened tissue and adjacent tissues. Thus irritation can occur, or the clip can be worked loose causing evisceration. Moreover, numerous clips must be employed for high strength fastening, due to the small area over which force is applied.

Another fastener used in joining tissues has the form of an adhesive strip. The strip extends across an incision, thus holding the wound closed. A limitation of this device is that it is not appropriate for the fastening of internal structures. Further, the fastener lacks sufficient strength for high stress applications.

One of the most common tissue fasteners are thread sutures. These fasteners are installed by sewing the suture through the structures to be fastened. A disadvantage to sutures lies in the relatively great amount of time required for installation. Installation delays result in high operating room costs and increased patient trauma. Moreover, while these sutures may be installed in biodegradable (dissolvable) form, they dissolve fairly rapidly, making their use unsuitable in applications where fastening strength must be maintained over longer time periods.

Thus, it is an object of the invention to provide a method of fastening which is rapid and which renders high initial levels of fastening strength (tensile strength).

It is an additional object to provide a method of fastening which may be used for internal application, without requiring extensive surgery.

It is yet another object of the invention to provide a method of fastening in which the fastener becomes firmly anchored in the fastened structures and avoids protuberances into neighboring interstitial areas.

SUMMARY OF THE INVENTION

In accordance with the invention, the fastener comprises a connecting member and two opposing heads having non-coplanar ends, that is, ends defining non-parallel planes. The head ends have acute angles which share a common ray, thus forming opposing pointed ends. The heads may be provided with a variety of cross-sectional configurations, while in a preferred embodiment, the heads have a cylindrical cross-section, and are trapeziform or trapezoidal in shape.

In accordance with one embodiment of the invention, the fasteners are installed by being driven through needles having slotted bores. The needles pierce the layers to be fastened, and the heads are urged down the needle bores via rods. In one embodiment, the heads are provided with a flattened profile to receive securely the rod end.

According to another aspect of the invention, the fasteners are used to join resilient or conformable layers. The heads are drawn into the conformable layers, whereupon the opposing pointed ends become embedded therein. Thus, protuberance is minimized, and the head is more securely positioned.

In accordance with a further aspect of the invention, fasteners according to the invention are used to join biological tissues, as in medical applications. Of particular advantage is the embedment of the opposing pointed ends in the fastened tissue, wherein irritation through contact with adjacent structure is minimized. Further, the fasteners may be fabricated from biodegradable materials, thus allowing for natural healing. Due to the relatively high mass of the fastener, as compared to common sutures, loss of fastening strength through degradation is delayed.

In accordance with yet another aspect of the invention, the fastener is installed with elongated needles, stabilized by a channel through which the connector passes. An arthroscope may be used in conjunction with the elongated needles for purposes of non-invasive surgical fastening.

BRIEF DESCRIPTION OF THE DRAWINGS

Other aspects of the invention will become apparent after considering several illustrative embodiments taken in conjunction with the drawings in which:

FIGS. 2 and 3 are plan views of two embodiments of fasteners of the invention;

FIGS. 4-9 are cross sectional views showing various head configurations in accordance with the invention.

FIG. 4 is a schematic view of a sequence of operations in installing the fastener shown in FIG. 2;

FIG. 5 is a schematic view of a sequence of operations in installing the fastener shown in FIG. 3;

FIG. 6A is a cross-sectional view of a knee joint taken along line 6A—6A of FIG. 6B, showing a fastener in accordance with the invention fastening a tear in the medial meniscus;

FIG. 7 is a perspective view of a fastener installation apparatus in accordance with the invention;

FIG. 8 is a plan view of an assemblage of fasteners of the type shown in FIG. 3.

DETAILED DESCRIPTION OF THE INVENTION

With reference to FIGS. 1-7, the invention provides for the fastening of layers of material, wherein the fastener 10 has two opposing heads 14a, 14b having pointed ends which are embedded in the material when installed.

Figure 1:
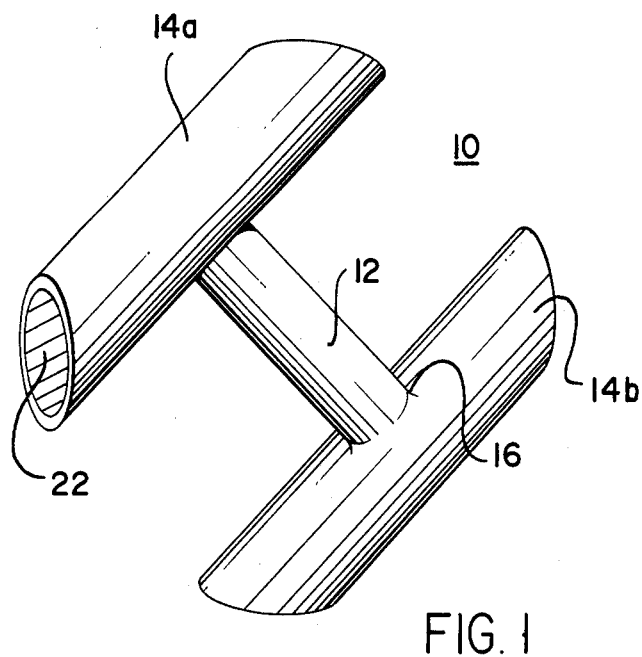
FIG. 1 is a perspective view of a fastener in accordance with the invention.
Figure 11:
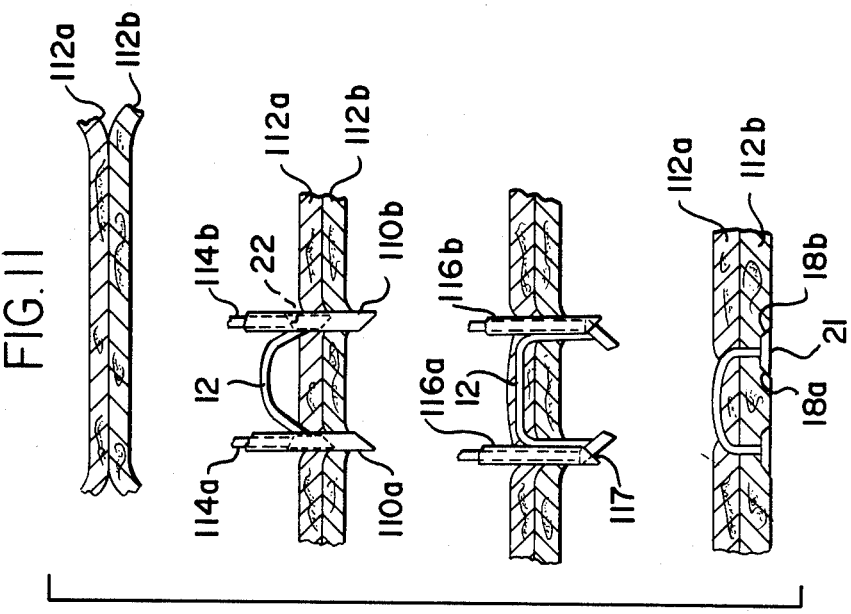
Figure 10:
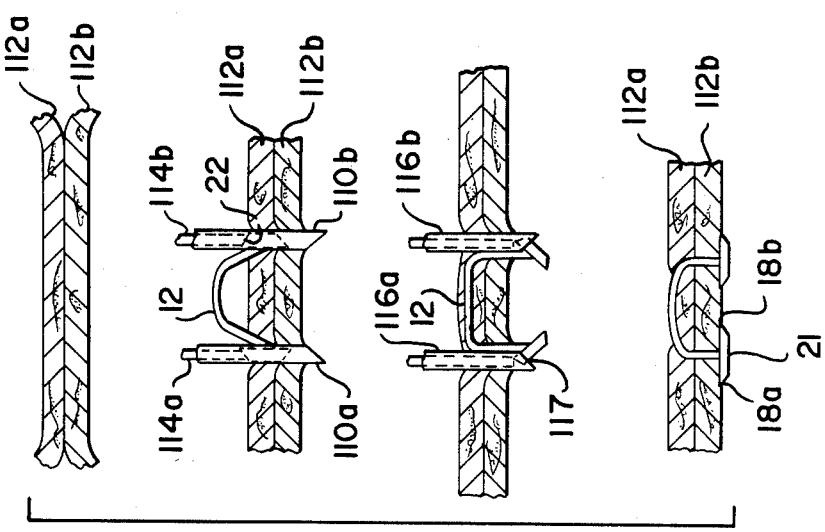
Figure 13:
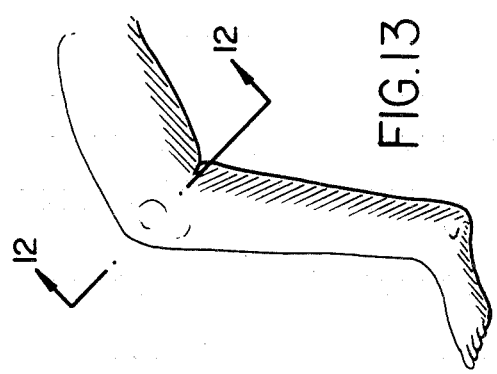
Figure 12:
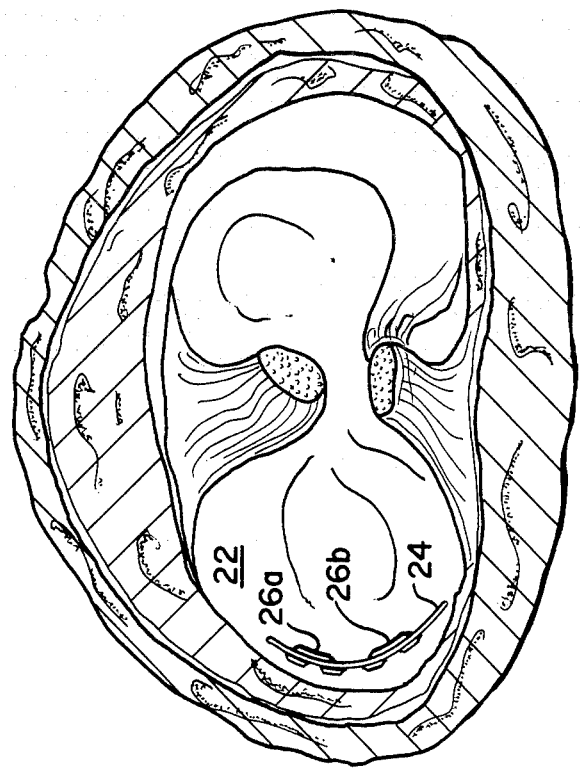
Figure 14:
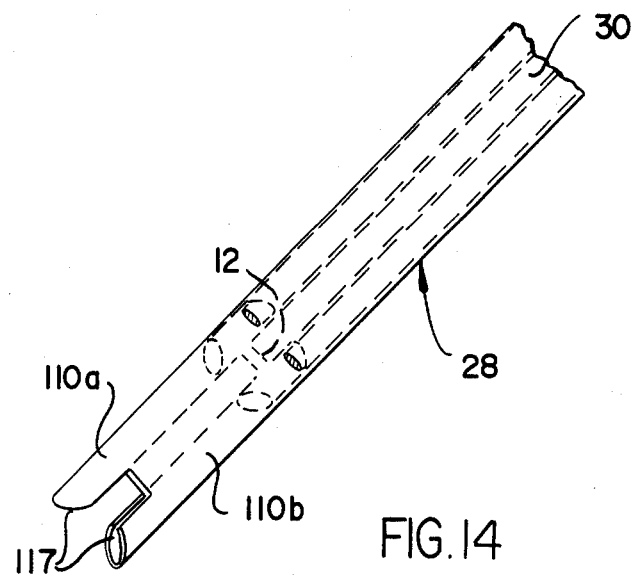
Figure 15:
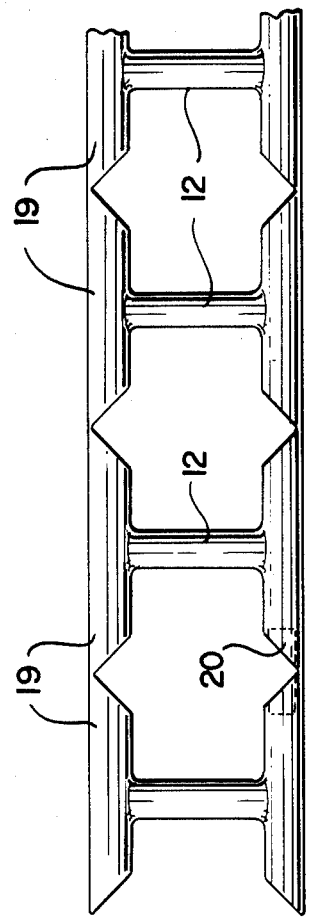

FIG. 1 shows a preferred embodiment of the invention, which comprises a connecting member 12, which may be bar shaped, coupled to two heads 14a, 14b. The fastener is integrally fabricated, as in a mold, with a radial expansion 16 between connecting bar 12 and heads 14a, 14b.

With reference to FIG. 2, it can be seen that heads 14a, 14b are provided with a plurality of ends, preferably two, defining non-parallel planes, 16a, 16b having acute angles 18a, 18b which share a common ray 19. These acute angles are of less than 60 degrees to the longitudinal axis of the head members. In FIG. 2, angles 18a, 18b are disposed closest to the connecting bar 12, while in FIG. 3, they are furthest away from connecting bar 12. Thus, the heads may be trapeziform, or trapezoidal in shape. Various cross-sectional shapes are shown in FIGS. 4–9, taken along line 3A—3A of FIG. 2.

With reference to FIGS. 4 and 5, the fastener 10 of the invention may be installed by driving heads 14a, 14b through needles 110a, 110b having a slotted bore. Connecting bar 12 extends through slots 116a, 116b. Needles 110a, 110b have sharpened ends which pierce through layers 112a, 112b, whereupon rods 114a, 114b urge heads 14a, 14b down the needle bore. For proper rod/head contact, heads 14a, 14b may be provided with recesses 20 sized to securely engage the rod end. As heads 14a, 14b emerge from needles 110a, 110b, the heads toggle in the direction of the opened needle profile 117. After rods 114a, 114b have driven heads 14a, 14b completely out of the needle bore, the needles are withdrawn. Heads 14a, 14b lie flat against layer 112b, and are drawn inwards by a resilient force exerted via connecting bar 12, and through pressure exerted by the joined layers.

The fasteners of the present invention are advantageously employed in the joining of a plurality of layers, where the layer facing installed heads 14a, 14b is resilient or conformable. The fasteners can thus be employed to avoid protuberances at the joined area. If layer 112b is rubber, for example, heads 14a, 14b are drawn inwardly into layer 112b. Heads 14a, 14b are more securely anchored by points 18a, 18b, which become embedded within the layer material.

The fasteners of the present invention are particularly useful in medical applications, where it is desired to fasten biological structures such as layers of tissue, cartilage, and or bone. As shown in FIGS. 4(d) and 5(d), points 18a and 18b are embedded in tissue layers, 112b. A countersinking effect is realized, wherein the fastener heads 14a, 14b are partially (FIG. 4(d)) or wholly (FIG. 5(d)) disposed within layer 112b. In surgical applications, exposed sharp edges may cause irritation, particularly where other tissue layers contact the heads 14a, 14b. To minimize protuberances, therefore, profile 20 may be provided with rounded edges 21a, 21b.

An illustrative surgical application is shown in FIG. 6, depicting the medial and lateral meniscus of the knee, in cross section taken along line 6A—6A of FIG. 6B. The medial meniscus 22 has been torn. The tear 24 is shown repaired with fasteners 26a, 26b. The tear edges may be considered as layers 112a, 112b of FIG. 4. Arthroscopy may be employed in combination with elongated installation needles 28, such as are shown in FIG. 7. The needles are formed from a tube, longitudinally compressed to form a channel 30, through which connecting bar 12 may pass. Channel 30 additionally serves to rigidize the elongated needles, and to maintain same in proper spaced relationship.

The fasteners may be fabricated from elastomers or plastics, including polyurethane, polyvinylchloride and NYLON (a polyamide polymer) and its derivatives, including nylon 66. For surgical applications, a biodegradable material may be used, wherein the fasteners are fabricated from materials including: Polylactic acids (and its isomers); polyglycolic acid; polydioxanone; or polyglactin. Due to the greater mass of the fasteners of the invention, as compared to common thread sutures, biodegradation can be extended over a longer time period. Hence, where the fastened tissues are poorly vascularized, fastening strength can be maintained over a longer time period, thus enabling the use of biodegradable materials in a wider range of applications.

The fasteners of the present invention may be of greatly varying size, depending on the particular use to which they will be applied. Typically, the length of connecting bar 12 is in the range of 5.0 to 80.0 mm. Typical head and connecting bar thickness ranges from 0.3–3.0 mm. It should be understood, however, that size may vary far beyond these ranges.

Fasteners, according to the invention, may be provided as continuously molded stock, or in assemblages of connected fasteners, for example assemblages of ten fasteners. FIG. 8 illustrates the fastener of FIG. 2A connected at points 18a and 18b. The installation apparatus severs the individual fasteners prior to installation, as described, for example, in U.S. Pat. No. 4,039,078.

Additionally, fasteners, according to the invention, may be stretched to reorient the molecular structure of connecting bar 12, thus providing greater levels of tensile strength. Stretching may be performed during the fastener manufacturing process either in-mold or out of mold, with the introduction of external heat or without, as the particular application requires.

While various aspects of the invention have been set forth by the drawings and the specification, it is to be understood that the foregoing detailed description is for illustration only and that various changes in parts, as well as the substitution of equivalent constituents for those shown and described, may be made without departing from the spirit and scope of the invention as set forth in the appended claims.

What is claimed is:

1. The method of fastening material comprising:
   Providing a fastener having an elongated connector with a head on one end having end faces in non-parallel planes;
   Inserting a slotted hollow needle into the material;
   Inserting the head in one end of said needle with said connecting member extending through the slot in said needle; and
   Driving said head through and out of the other end of said needle and into said material; said head being driven through said needle by being provided with an aperture disposed to securely receive a driving rod.

2. The method of claim 1 wherein said head is provided with a trapezium cross section.

3. The method of claim 1 wherein said head is provided with a trapezoidal cross section.

4. The method of claim 1 wherein said connecting member has an end which expands radially outwards to join with said head member.

5. The method of claim 1 wherein said connecting member is stretched during insertion into said material.

6. The method of claim 1 wherein said head member is provided with ends that define acute angles of less than 60 degrees to the longitudinal axis of said head member.

7. The method of claim 1 wherein said head member is provided with ends that define acute angles to the longitudinal axis of said head member and which share a common ray.

8. The method of claim 1 including providing a fastener fabricated from a material selected from the class consisting of polyamide polymers, polylactic acid and its isomers, polyglycolic acid, polydioxanone, and polyglactin.

9. The method of claim 1 including contacting of said end faces to drive said head member through said needle.

10. The method of claim 1 wherein said driving rod contacts a platform in said aperture of said end face.

11. The method of fastening layers, comprising the steps of:
   inserting two needles having slotted bores through the layers to be fastened;
   driving the heads of a fastener through the needles, where the heads have non-coplanar ends, and are connected to each other through the respective needle slots by a filament, said heads being driven through said needles by being provided with apertures to receive respective driving rods; and
   removing the needles with the fastener embedded in the material.

12. Method of claim 11, wherein the layers are biologic.

* * * * *